United States Patent
YI

(10) Patent No.: US 11,680,233 B2
(45) Date of Patent: Jun. 20, 2023

(54) NUCLEIC ACID EXTRACTION AND PURIFICATION DEVICE AND BIOCHEMICAL MOLECULE EXTRACTION AND PURIFICATION DEVICE

(71) Applicant: WUHAN EDEBIO TECHNOLOGY LLC., Hubei (CN)

(72) Inventor: Chuli YI, Wuhan (CN)

(73) Assignee: WUHAN EDEBIO TECHNOLOGY LLC., Wuhan (CN)

( * ) Notice: Subject to any disclaimer, the term of this patent is extended or adjusted under 35 U.S.C. 154(b) by 289 days.

(21) Appl. No.: 16/971,652

(22) PCT Filed: Mar. 11, 2019

(86) PCT No.: PCT/CN2019/077621
§ 371 (c)(1),
(2) Date: Aug. 20, 2020

(87) PCT Pub. No.: WO2019/174539
PCT Pub. Date: Sep. 19, 2019

(65) Prior Publication Data
US 2020/0392437 A1    Dec. 17, 2020

(30) Foreign Application Priority Data

Mar. 13, 2018  (CN) .................. 201820346718.X
Dec. 20, 2018  (CN) .................. 201822153615.4

(51) Int. Cl.
*B01D 63/06* (2006.01)
*C12M 1/26* (2006.01)
(Continued)

(52) U.S. Cl.
CPC .......... *C12M 1/12* (2013.01); *B01D 29/0009* (2013.01); *B01D 29/03* (2013.01); *B01D 63/06* (2013.01);
(Continued)

(58) Field of Classification Search
CPC .............. B01D 29/03; B01D 29/0009; B01D 2201/02; B01D 63/06; C12M 1/12; C12M 33/14; C12N 15/1017; G01N 2030/8827
See application file for complete search history.

(56) References Cited

U.S. PATENT DOCUMENTS

| 6,153,425 A | * | 11/2000 | Kozwich | ............... B01L 3/5082 |
| | | | | 435/306.1 |
| 9,145,581 B1 | * | 9/2015 | Lai | ........................ C12Q 1/6806 |
| 2012/0052588 A1 | * | 3/2012 | Rupprecht | ............. G01N 31/22 |
| | | | | 436/128 |

FOREIGN PATENT DOCUMENTS

| CN | 106086003 | 11/2016 |
| CN | 207031418 | 2/2018 |
| CN | 208414378 | 1/2019 |

OTHER PUBLICATIONS

CN 106086003 machine translation.*
PCT International Search Report, PCT/CN2019/077621, dated May 8, 2019, 10 Pages.

* cited by examiner

*Primary Examiner* — Benjamin L Lebron
(74) *Attorney, Agent, or Firm* — Fenwick & West LLP

(57) ABSTRACT

Provided are a nucleic acid extraction and purification device and a biochemical molecule extraction and purification device, belonging to the field of experimental supplies. Both devices have the functionality of a test tube, and thus can hold a liquid to perform preprocessing extraction and purification of nucleic acids or biochemical molecules such as nucleic acids, i.e. achieving a process of cell rupture. Furthermore, both devices can quickly and easily transfer liquid to the extraction membrane, achieving the extraction and purification of nucleic acids or biochemical molecules such as nucleic acids. Furthermore, the two devices do not need to manually fit with a pipettor during the process of (Continued)

liquid transfer or use an automated robotic arm and a mechanical pipettor to complete the process of liquid transfer.

11 Claims, 11 Drawing Sheets

(51) Int. Cl.
*B01D 29/00* (2006.01)
*C12M 1/12* (2006.01)
*C12N 15/10* (2006.01)
*B01D 29/03* (2006.01)
*G01N 30/88* (2006.01)

(52) U.S. Cl.
CPC ......... *C12M 33/14* (2013.01); *C12N 15/1017* (2013.01); *B01D 2201/02* (2013.01); *G01N 2030/8827* (2013.01)

NUCLEIC ACID EXTRACTION AND PURIFICATION DEVICE AND BIOCHEMICAL MOLECULE EXTRACTION AND PURIFICATION DEVICE

CROSS-REFERENCE TO RELATED APPLICATIONS

This application is the National Stage of International Application No. PCT/CN2019/077621, filed Mar. 11, 2019, which claims the right of priority based on CN application no. 201820346718.X, filed Mar. 13, 2018, and CN application no. 201822153615.4, filed Dec. 20, 2018, each of which is herein incorporated in its entirety by reference.

FIELD

The present application relates to the technical field of experimental supplies, and in particular to a nucleic acid extraction and purification device and a biochemical molecule extraction and purification device.

BACKGROUND

Nucleic acid is a biological macromolecular compound polymerized by many nucleotides, and is widely present in all animal and plant cells and microorganisms. The application of nucleic acid is very extensive. Column methods are generally adopted to extract and purify nucleic acids from biological tissues.

The principle of the existing column method for nucleic acid extraction is that, the impurities in the nucleic acid solution to be extracted is filtered out by a filter column, the nucleic acids are absorbed by an absorption column, and the absorbed nucleic acids are then rinsed and eluted to obtain the extracted and purified nucleic acids. The process is as follows: firstly, liquid cells and various chemical reagents (such as cell lysis solution and nucleic acid release solution) are added into a test tube, mixed evenly, and then left to stand still until the liquid cells are ruptured and the nucleic acids in the cells are released into the solution to form a nucleic acid solution to be extracted; secondly, the nucleic acid solution to be extracted is transferred from the test tube to the nucleic acid filter column or the absorption column; the filter column and the absorption column are respectively provided with a nucleic acid filter membrane and an absorption membrane, impurities in the nucleic acid solution to be extracted are filtered out by the filter column or the nucleic acids are absorbed by the absorption column, to obtain extracted nucleic acids. The extracted nucleic acids are then subjected to subsequent rinsing and elution so as to be purified.

The inventor found that the prior art has at least the following problems. In the existing column method, the nucleic acid solution to be extracted needs to be transferred from a test tube to a filter column or an absorption column. The transfer process of the nucleic acid solution often requires manual cooperation with pipettes. However, manual pipetting increases the workload of operators and requires certain accuracy. To replace the manual labor and realize the automation of nucleic acid purification, it needs to be completed by an automated robotic arm or mechanical pipette. However, the existing robotic arms or mechanical pipettes make the automated instrument large in volume, heavy in mass, less efficient and costly to use.

SUMMARY

In order to solve the problems in the prior art that manual pipetting increases the workload of the operators and the automated instrument for automated pipetting has a large volume, heavy weight, low efficiency, and high cost of use, a nucleic acid extraction and purification device and a biochemical molecule extraction and purification device are provided according to the present application.

The nucleic acid extraction and purification device according to the present application includes a nucleic acid purification column. A purification column liquid inlet is provided at the top of the nucleic acid purification column, a purification column liquid outlet is provided at the bottom of the nucleic acid purification column, and a nucleic acid extraction membrane is provided in the nucleic acid purification column. The nucleic acid extraction and purification device further includes a breakable member. The breakable member is arranged between the purification column liquid inlet and the nucleic acid extraction membrane, and is arranged in the nucleic acid purification column. The breakable member is provided with a groove. The nucleic acid extraction and purification device further includes a piercing rod for piercing the breakable member.

Specifically, the groove includes an annular groove arranged at the center of the breakable member, and multiple support legs are provided on the bottom surface of the breakable member on the annular groove.

Specifically, the groove includes multiple strip-shaped grooves arranged along the radius of the breakable member.

Specifically, the groove includes an annular groove and multiple strip-shaped grooves. The annular groove is arranged at the center of the breakable member, the multiple strip-shaped grooves are arranged between the annular groove and an outer wall of the breakable member and are arranged along the radius of the breakable member, and multiple support legs are arranged on the bottom surface of the breakable member on the annular groove.

Moreover, the nucleic acid extraction and purification device further includes a support member. The support member is hermetically installed on an inner wall of the nucleic acid purification column, and the breakable member is fixed to the support member.

Specifically, the support member is a cylinder, or a round sheet with a hole in the middle, or a round basin with a basin bottom facing upward and a hole in the middle of the basin bottom. The breakable member is sheet-shaped, and is bonded with the support member by a hot melting technique.

Specifically, the support member includes a round basin with a basin bottom facing upward and a hole in the middle of the basin bottom, and further includes a snap ring. The snap ring includes an annular body and an annular snap protrusion arranged on the outer periphery of the annular body. A peripheral wall of the round basin is provided with an annular snapping groove adapted to the annular snapping protrusion, and the snap ring is snapped and installed in the round basin. The breakable member is sheet-shaped, and is clamped between an upper end surface of the annular body and a lower end surface of the basin bottom.

Specifically, one of the lower end surface of the basin bottom and the upper end surface of the annular body is provided with an annular groove, and the other is provided with a protrusion adapted to the annular groove. The breakable member is provided with a bulging portion adapted to the annular groove, and the protrusion presses the bulging portion into the annular groove.

Specifically, an inner edge of the upper end surface of the basin bottom is inclined downward relative to an outer edge of the upper end surface, and an inner edge of the lower end surface of the annular body is inclined upward relative to an outer edge of an outer edge of the lower end surface.

Moreover, the nucleic acid extraction and purification device further includes a mounting column. The mounting column is sleeved on the inner wall of the nucleic acid purification column. The breakable member is provided on the mounting column and located above the nucleic acid extraction membrane.

Specifically, the bottom of the piercing rod has a conical structure, a lower part of the piercing rod is sleeved with a stirring sheet, and an outer diameter of the stirring sheet is smaller than an inner diameter of the nucleic acid purification column.

Specifically, the breakable member may be a polypropylene breakable member, a polyethylene breakable member, a polytetrafluoroethylene breakable member, an acetate breakable member, a nitrocellulose breakable member, a regenerated fiber breakable member or a special paper breakable member.

Specifically, the ration of the depth of the groove to the thickness of the breakable member is 100:(101 to 1150).

Further, the ratio of the depth of the groove to the thickness of the breakable member is 100:110.

The beneficial effects of the nucleic acid extraction and purification device provided by the present application are as follows. Before the breakable member is pierced, the nucleic acid purification column has the function of a test tube, so that the nucleic acid purification column can contain liquid to realize pretreatment of nucleic acid extraction and purification, namely the process of cell rupture. After the breakable member is pierced, a hole is formed in the breakable member, the liquid containing nucleic acids flows down through the hole, and the nucleic acids are extracted and purified by the nucleic acid extraction membrane. In this process, the liquid is transferred from the breakable member to the nucleic acid extraction membrane, thus realizing rapid and simple transfer of the liquid. In the device, the liquid transfer process neither requires manual cooperation with a pipette nor an automated robotic arm or a mechanical pipette to complete the liquid transfer process. The nucleic acid extraction and purification device greatly reduces the cost of nucleic acid extraction and accelerates the extraction and purification. Compared with manual pipetting, the workload of operators on nucleic acid extraction and purification is reduced. Compared with an automated robotic arm or a mechanical pipette, the nucleic acid extraction and purification device provided according to the present application is small and light, so that the pipetting process of nucleic acid extraction and purification is simple and automated, thereby greatly improving the efficiency of nucleic acid extraction and purification.

The biochemical molecule extraction and purification device provided by the present application includes an extraction column, an extraction membrane, a liquid temporary blocking mechanism and an execution member. An extraction column inlet is provided at one end of the extraction column, and an extraction column outlet is provided at the other end of the extraction column. The extraction membrane and the liquid temporary blocking mechanism are both arranged in the extraction column. The liquid temporary blocking mechanism is located between the extraction column liquid inlet and the extraction membrane. The liquid temporary blocking mechanism includes a horizontal supporting portion and at least one detachable portion. The horizontal supporting portion is retained on an inner wall of the extraction column. The horizontal supporting portion is provided with at least one mounting hole, and the number of mounting holes is the same as the number of the detachable portions. One detachable portion is provided in each mounting hole. The detachable portion is matched with the execution member and can be detached from the corresponding mounting hole under the action of the execution member.

Optionally, the detachable portion is a round plug, and the horizontal supporting portion is a cylinder.

Optionally, the liquid temporary blocking mechanism further includes an outer longitudinal supporting portion, wherein the outer longitudinal supporting portion is fixed outside the horizontal supporting portion and is perpendicular to the horizontal supporting portion. The horizontal supporting portion is retained on the inner wall of the extraction column by the outer longitudinal supporting portion.

Optionally, the detachable portion is sheet-shaped, and multiple discontinuous first strip-shaped holes are provided between the detachable portion and the horizontal supporting portion.

Optionally, the detachable portion is a round sheet, and multiple discontinuous second strip-shaped holes are provided on the detachable portion in a radial direction.

Optionally, the detachable portion includes a first outer ring and a first inner ring, wherein the first outer ring is radially provided with the multiple discontinuous second strip-shaped holes, and multiple discontinuous third strip-shaped holes are arranged between the first outer ring and the first inner ring.

Optionally, the widths of the first strip-shaped hole, the second strip-shaped hole, and the third strip-shaped hole are all less than or equal to 0.2 millimeters.

Optionally, the horizontal supporting portion is a round sheet, the outer longitudinal supporting portion includes an upper ring and a lower ring, and the horizontal supporting portion is clamped between the upper ring and the lower ring.

Optionally, the detachable portion is a round plug, the horizontal supporting portion is a round sheet, and the liquid temporary blocking mechanism further includes an inner longitudinal supporting portion. The inner longitudinal supporting portion is arranged inside the outer longitudinal supporting portion. The inner longitudinal supporting portion is fixed to the inner ring of the horizontal supporting portion and is perpendicular to the horizontal supporting portion. The inner longitudinal supporting portion is a cylinder, and the detachable portion is retained in the inner longitudinal supporting portion.

Optionally, the inner longitudinal supporting portion is a bottom-sealed cylinder, the detachable portion is retained at an opening of the inner longitudinal supporting portion, and an inner wall of the inner longitudinal supporting portion is provided with at least one window hole.

The beneficial effects of the biochemical molecule extraction and purification device provided by the present application are as follows. By providing the liquid temporary blocking mechanism, which includes the horizontal supporting portion and at least one detachable portion installed in the corresponding mounting hole on the horizontal supporting portion, between the extraction column liquid inlet and the extraction membrane, the liquid temporary blocking mechanism and the extraction column form a liquid storage cavity while each detachable portion is located in the corresponding mounting hole, the extraction column has the function of a test tube, so that the device can contain liquid to realize pretreatment of nucleic acid extraction and purification, namely the process of cell rupture. After the detachable portion is detached from the corresponding mounting hole under the action of the execution member, the corresponding mounting hole forms a leakage hole, the liquid containing nucleic acids flows down through the leakage hole, and the nucleic acids are extracted and purified by the extraction membrane. In this process, the liquid is transferred from the liquid storage cavity to the extraction membrane, thus realizing rapid and simple transfer of the liquid. In the device, the liquid transfer process neither requires manual cooperation with a pipette nor an automated robotic arm or a mechanical pipette to complete the liquid transfer process. The device greatly reduces the cost of nucleic acid and other molecule extraction and accelerates the extraction and purification. Compared with manual pipetting, the workload of operators on nucleic acid extraction and purification is reduced, and the difficulty of nucleic acid extraction and purification is reduced too. Besides, the device is small, light, and cost saving, thereby improving the efficiency of nucleic acid extraction and purification.

BRIEF DESCRIPTION OF THE DRAWINGS

In order to more clearly illustrate technical solutions of the present application, the drawings used in the description of the embodiments are briefly described below. It is apparent that the drawings in the following description show only some embodiments of the present application, and other drawings may be obtained by those skilled in the art based on the drawings without any creative efforts.

Figure 1:
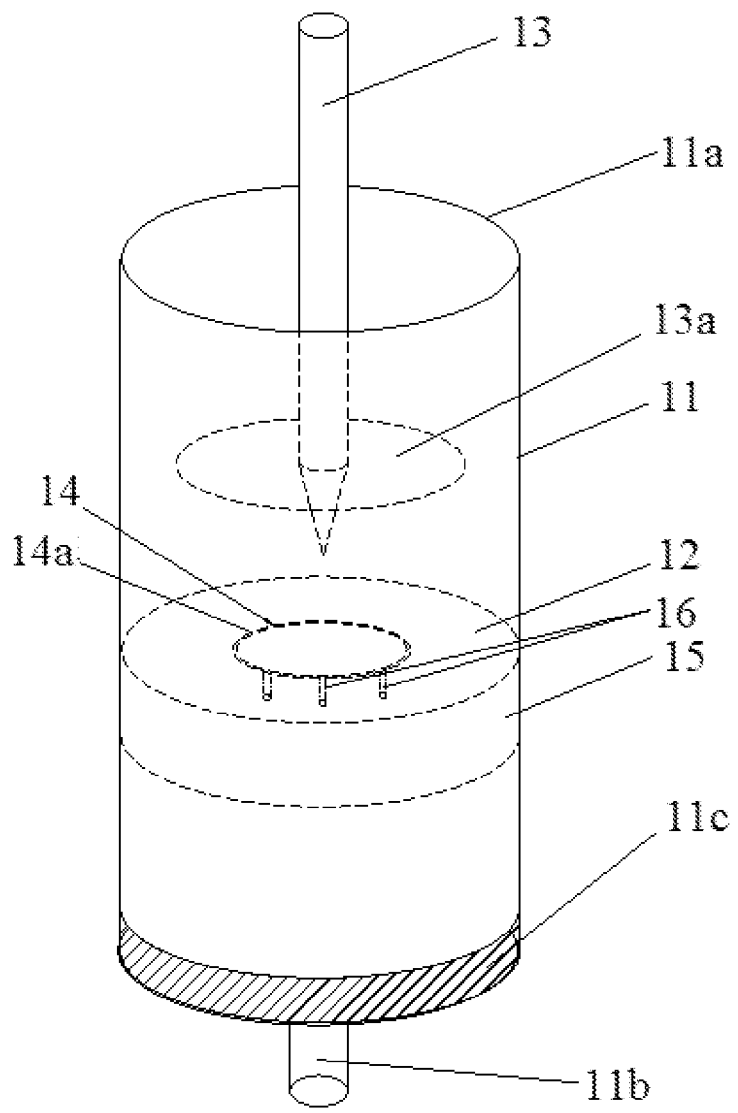
FIG. 1 is a schematic structural view of a nucleic acid extraction and purification device provided by an embodiment of the present application.

Reference numerals of the components are listed as follows:

11 nucleic acid purification column, 11a purification column liquid inlet, 11b purification column liquid outlet, 11c nucleic acid extraction membrane, 12 breakable member, 13 piercing rod, 13a stirring sheet, 14 groove, 14a annular groove, 14b strip-shaped groove, 15 support member, 16 support leg, 17 mounting column, 18 round basin, 181 annular snapping groove, 19 snap ring, 191 annular body, 192 annular snapping protrusion;

21 extraction column, 21a extraction column liquid inlet, 21b extraction column liquid outlet, 21c mounting hole, 22 extraction membrane, 23 liquid temporary blocking mechanism, 231 horizontal supporting portion, 231f inner longitudinal supporting portion, 231g window hole, 232 detachable portion, 232b first strip-shaped hole, 232c first outer ring, 232d first inner ring, 232f second strip-shaped hole, 232g third strip-shaped hole, 24 execution member, 25 outer longitudinal supporting portion.

DETAILED DESCRIPTION OF THE EMBODIMENTS

In order to make objects, technical solutions and advantages of the present application clearer, the embodiments of the present application are further described below in conjunction with the accompanying drawings.

Embodiments of the nucleic acid extraction and purification device (referring to FIGS. 1 to 5).

As shown in FIG. 1, the nucleic acid extraction and purification device includes a nucleic acid purification column 11 and a breakable member 12. A purification column liquid inlet 11a is provided at the top of the nucleic acid purification column 11, a purification column liquid outlet 11b is provided at the bottom of the nucleic acid purification column 11, and a nucleic acid extraction membrane 11c is provided in the nucleic acid purification column 11. The breakable member 12 is arranged between the purification column liquid inlet 11a and the nucleic acid extraction membrane 11c, and is arranged in the nucleic acid purification column 11. The breakable member 12 is provided with a groove 14. The nucleic acid extraction and purification device further includes a piercing rod 13 for piercing the groove 14. In this embodiment, the nucleic acid purification column 11 may be cylindrical. The nucleic acid extraction membrane 11c may be a filter membrane or an absorption membrane. The piercing rod 13 can be used alone.

Specifically, the groove 14 includes an annular groove 14a arranged at the center of the breakable member 12, and multiple support legs 16 are provided on the bottom surface of the breakable member 12 in the annular groove 14a. Each of the support legs 16 is longer than 0.1 mm. The user can stab the breakable member 12 with the piercing rod 13. Since the thickness of the breakable member 12 at the groove 14 is obviously smaller than the thickness of other parts of the breakable member 12, it is easy for the breakable member 12 enclosed inside the annular groove 14a to be partially or completely separated from the breakable member 12 enclosed outside the annular groove 14a by the annular groove 14a after being stressed, thus forming a through hole for liquid to pass through. The annular groove 14a can be used in experiments suitable for less liquid cells and various chemical reagents, and processing of the annular groove 14a is simple. When the piercing rod 13 completely separates the breakable member 12 inside the annular groove 14a from the rest of the breakable member 12 by the annular groove 14a, the breakable member 12 inside the annular groove 14a falls off and covers the nucleic acid extraction membrane 11c, thereby hindering the liquid from passing through the nucleic acid extraction membrane 11c. The detached breakable member 12 can be kept at a certain distance from the nucleic acid extraction membrane 11c by the multiple support legs 16, thereby preventing the detached breakable member 12 from hindering the liquid from passing through the nucleic acid extraction membrane 11c.

Figure 2:
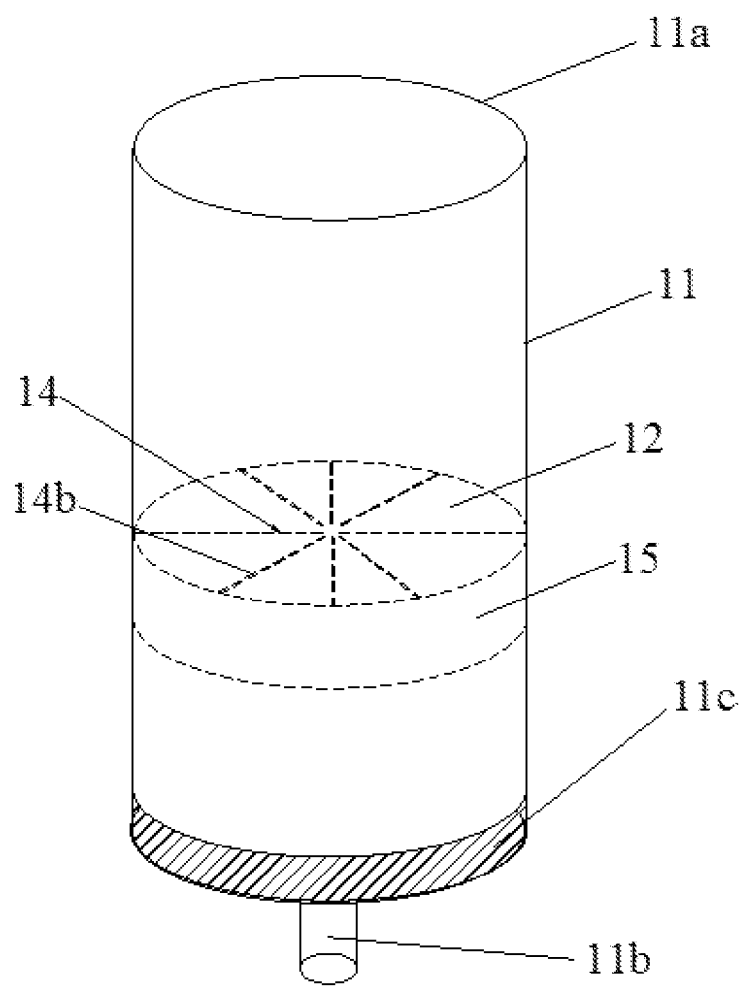
FIG. 2 is a schematic structural view of the nucleic acid extraction and purification device provided by an embodiment of the present application, wherein the grooves are strip-shaped grooves.

Specifically, as shown in FIG. 2, the groove 14 includes multiple strip-shaped grooves 14b arranged along the radius of the breakable member 12. The user can stab the breakable member 12 with the piercing rod 13. Since the thickness of the breakable member 12 at the groove 14 is obviously smaller than the thickness of other parts of the breakable member 12, the breakable member 12 can be easily ruptured by a single or multiple strip-shaped grooves 14b after being stressed, thus forming a passage for liquid to pass through. After ruptured at the strip-shaped groove 14b, the breakable member 12 does not fall, thereby avoid affecting the subsequent operation of the solution. The groove 14 can be used in experiments suitable for lots of liquid cells and various chemical reagents, and the groove 14 has a good ability to withstand stress.

Figure 3:
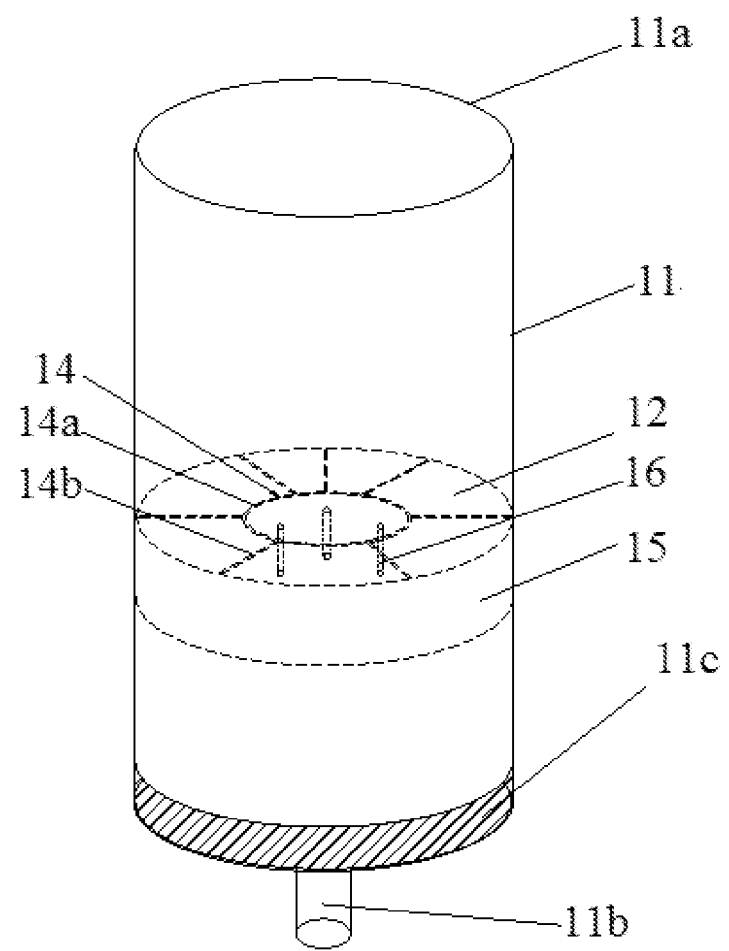
FIG. 3 is a schematic structural view of the nucleic acid extraction and purification device with grooves including annular grooves and strip-shaped grooves provided by an embodiment of the present application.

Specifically, as shown in FIG. 3, the groove 14 includes an annular groove 14a and multiple strip-shaped grooves 14b. The annular groove 14a is arranged at the center of the breakable member 12, the multiple strip-shaped grooves 14b are arranged between the annular groove 14a and an outer wall of the breakable member 12 and are arranged along the radius of the breakable member 12. Correspondingly, multiple support legs 16 are arranged on the bottom surface of the breakable member 12 on the annular groove 14a, and each of the multiple support legs 16 is longer than 0.1 mm. The intersection of the annular groove 14a and the multiple strip-shaped grooves 14b is very easy to be pierced through, such that the user can easily pierce the breakable member 12 through. The user can stab the breakable member 12 with the piercing rod 13. Since the thickness of the breakable member 12 at the groove 14 is obviously smaller than the thickness of other parts of the breakable member 12, the breakable member 12 can be easily ruptured by a single or multiple strip-shaped grooves 14b after being stressed, thus forming a passage for liquid to pass through. The groove 14 can be used in experiments suitable for a lot of liquid cells and various chemical reagents, and the groove 14 allows the liquid cells and various chemical reagents to pass through rapidly.

Moreover, as shown in FIG. 1, the nucleic acid extraction and purification device further includes a support member 15. The support member 15 is hermetically installed on an inner wall of the nucleic acid purification column 11, and the breakable member 12 is fixed to the support member 15. In this embodiment, the support member 15 and the breakable member 12 may be made of a same material, and the support member 15 and the breakable member 12 may be processed as a whole. In this embodiment, the breakable member 12 may be a thin plate or sheet, and the support member 15 and the breakable member 12 may be of an integral structure and integrally formed, or the breakable member 12 may be bonded with the support member 15 by a hot melting technique.

Specifically, the support member 15 may be a cylinder, or a circular sheet with a hole in the middle, or a round basin with a basin bottom facing upward and a hole in the middle of the basin bottom.

Figure 4:
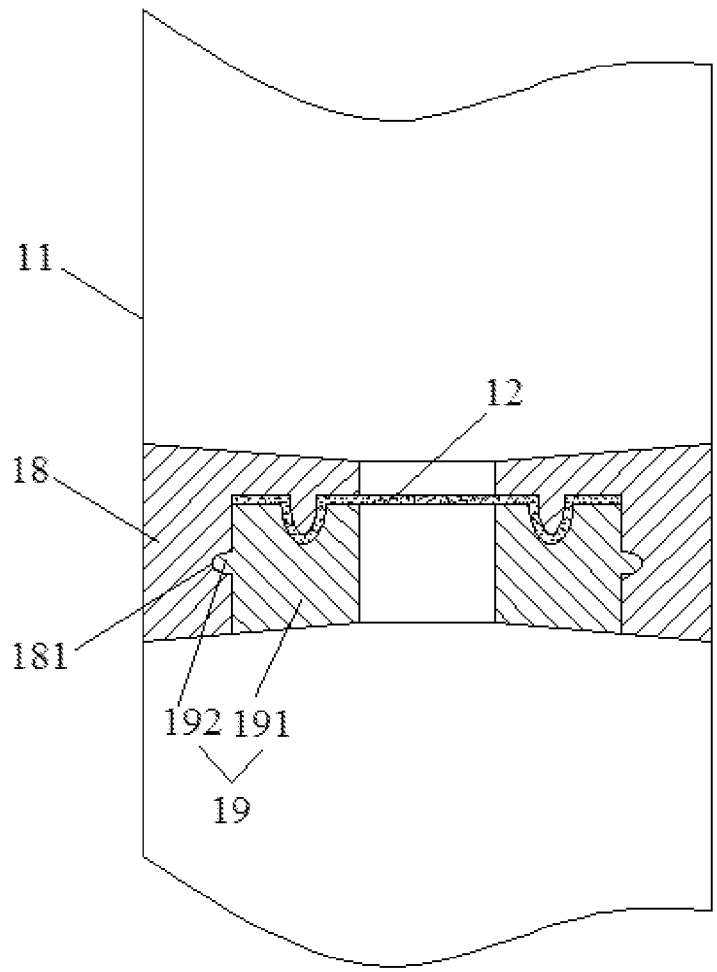
FIG. 4 is a schematic cross-sectional view of a breakable member provided by an embodiment of the present application cooperating with a first annular supporting portion and a second annular supporting portion.

Specifically, as shown in FIG. 4, the support member includes a round basin 18 with a basin bottom facing upward and a hole in the middle of the basin bottom, and further includes a snap ring 19. The snap ring 19 includes an annular body 191 and an annular snap protrusion 192 arranged on the outer periphery of the annular body. A peripheral wall of the round basin 18 is provided with an annular snapping groove 181 adapted to the annular snapping protrusion 192, and the snap ring 19 is snapped and installed in the round basin 18. In the snapped state, the annular snapping protrusion 192 is located in the annular snapping groove 181, and the outer peripheral surface of the annular body 191 is almost in contact with the peripheral wall of the round basin 18. The breakable member 12 is clamped between an upper end surface of the annular body 191 and a lower end surface of the basin bottom.

More specifically, one of the lower end surface of the basin bottom and the upper end surface of the annular body 191 (in FIG. 4, it is the snap ring) is provided with an annular groove, and the other (in FIG. 4, it is the basin bottom) is provided with a protrusion adapted to the annular groove. The breakable member is provided with a bulging portion adapted to the annular groove, and the protrusion presses the bulging portion into the annular groove. With this arrangement, the breakable member can be more firmly clamped between the two parts.

Specifically, an inner edge of the upper end surface of the basin bottom is inclined downward relative to an outer edge of the upper end surface, and an inner edge of the lower end surface of the annular body 191 is inclined upward relative to an outer edge of an outer edge of the lower end surface. With this arrangement, the liquid above the basin bottom can easily flow into the inner holes of the basin bottom and the annular body. Moreover, the liquid below the annular body can easily flow onto the inner wall of the nucleic acid purification column 11, and can thereby flow onto the nucleic acid extraction membrane 11c along the inner wall of the nucleic acid purification column 11.

Figure 5:
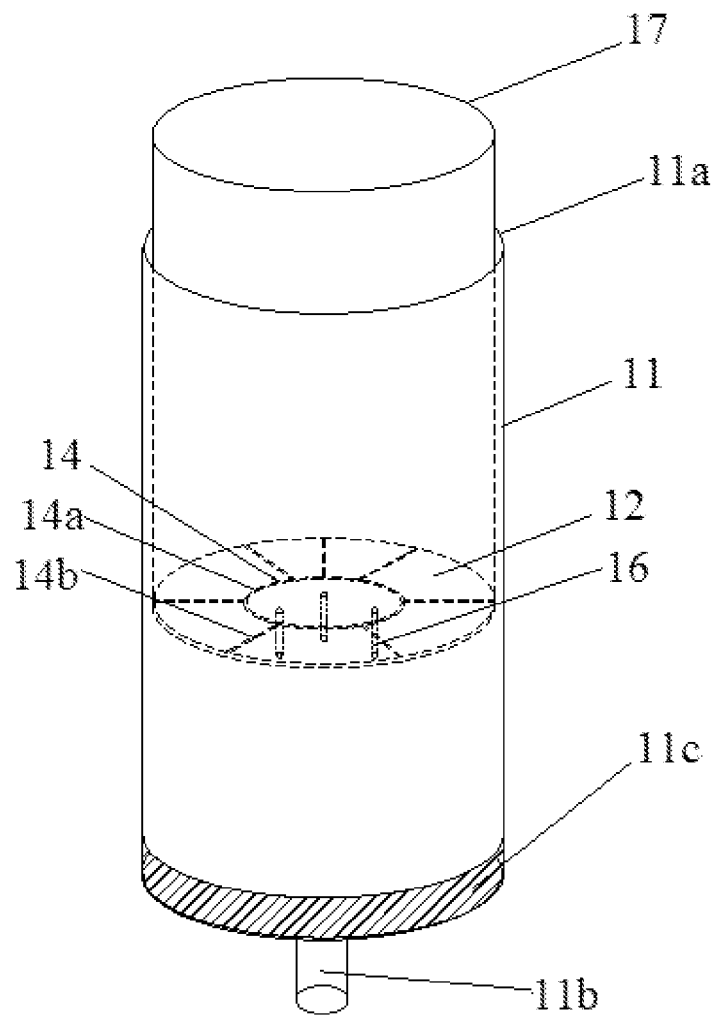
FIG. 5 is a schematic structural view of the breakable member provided by an embodiment of the present application cooperating with a mounting column.

Specifically, the breakable member 12 may be directly arranged on the nucleic acid purification column 11, that is, the breakable member 12 may be installed to the nucleic acid purification column 11, or the breakable member 12 may be indirectly arranged on the nucleic acid purification column 11. The specific method of indirect arrangement is as follows:

As shown in FIG. 5, the nucleic acid extraction and purification device further includes a mounting column 17, and the mounting column 17 is sleeved on the inner wall of the nucleic acid purification column 11. The breakable member 12 is installed on the mounting column 17 and located above the nucleic acid extraction membrane 11c. The mounting column 17 cooperates with the breakable member 12 to realize the function of a test tube. After the breakable member 12 is pierced by the piercing rod 13, the solution in the mounting column 17 can flow into the nucleic acid purification column 11, thus achieving the transfer of the solution. In this embodiment, the size of the outer wall of the mounting column 17 fits the inner wall of the nucleic acid purification column 11. While the piercing rod 13 pierces the breakable member 12, the mounting column 17 does not move relative to the nucleic acid purification column 11.

Specifically, the bottom of the piercing rod 13 has a conical structure, a lower part of the piercing rod 13 is sleeved with a stirring sheet 13a, and an outer diameter of the stirring sheet 13a is smaller than an inner diameter of the nucleic acid purification column 11. The conical structure is convenient for the piercing rod 13 to pierce the breakable member 12. Besides, before the breakable member 12 is pierced, the nucleic acid extraction column 1 cooperates with the breakable member 12 as a test tube (no water outlet at the bottom) to hold the liquid, so that various chemical reagents react with each other here, and the stirring sheet 13a can be used to mix well the liquid in the nucleic acid purification column 11.

Specifically, the breakable member 12 may be a polypropylene breakable member or a polyethylene breakable member. The polypropylene breakable member or polyethylene breakable member is safe and nontoxic. Since the polypropylene and polyethylene have good thermoplasticity, the polypropylene breakable member or polyethylene breakable member is easy to process.

Specifically, the ratio of the depth of the groove 14 to the thickness of the breakable member 12 is 100: (101 to 1150). With this arrangement, the user can easily pierce the breakable member 12. In this embodiment, the groove 14 may be formed on the top or bottom surface of the breakable member 12.

Further, the ratio of the depth of the groove 14 to the thickness of the breakable member 12 is 100:110. With this arrangement, it can be ensured that the breakable member 12 has a certain force-bearing capacity and the breakable member 12 is not ruptured before being pierced by the piercing rod 13, and due to the obvious difference between the depth of the groove 14 and the thickness of the breakable member 12, the groove 14 can be easily pierced.

The working principle of the nucleic acid extraction and purification device provided in this embodiment is briefly described in the following, which specifically is as follows:

The user adds liquid cells and various chemical reagents (such as cell lysis solution) into the nucleic acid purification column 11, mixes them well by the piercing rod 13 and then left them to stand still. After the cells are ruptured, the nucleic acids in the cells are released into the solution to form a nucleic acid solution to be extracted and purified. The breakable member 12 can be ruptured by the piercing rod 13, and after the breakable member 12 is ruptured, the nucleic acid solution to be purified flows down onto the nucleic acid extraction membrane 11c. Here, impurities are filtered out by the nucleic acid extraction membrane 11c (filter membrane) or nucleic acids are absorbed by the nucleic acid extraction membrane 11c (absorption membrane), and then the nucleic acid extraction membrane 11c is rinsed and eluted to extract the nucleic acids.

In the nucleic acid extraction and purification device provided by this embodiment of the present application, the nucleic acid purification column has the function of a test tube before the breakable member is pierced, so that the nucleic acid purification column can contain liquid to realize pretreatment of nucleic acid extraction and purification, namely the process of cell rupture. After the breakable member is pierced, a hole is formed in the breakable member, the liquid containing nucleic acids flows down through the hole, and the nucleic acids are extracted and purified by the nucleic acid extraction membrane. In this process, the liquid is transferred from the breakable member to the nucleic acid extraction membrane, thus realizing rapid and simple transfer of the liquid. In the device, the liquid transfer process neither requires manual cooperation with a pipette nor an automated robotic arm or a mechanical pipette to complete the liquid transfer process. The nucleic acid extraction and purification device greatly reduces the cost of nucleic acid extraction and accelerates the extraction and purification. Compared with manual pipetting, the workload of operators on nucleic acid extraction and purification is reduced. Compared with an automated robotic arm or a mechanical pipette, the nucleic acid extraction and purification device provided according to the present application is small and light, so that the pipetting process of nucleic acid extraction and purification is simple and automated, thereby greatly improving the efficiency of nucleic acid extraction and purification.

Embodiments of the biochemical molecule extraction and purification device (referring to FIGS. 6 to 15).

Figure 6:
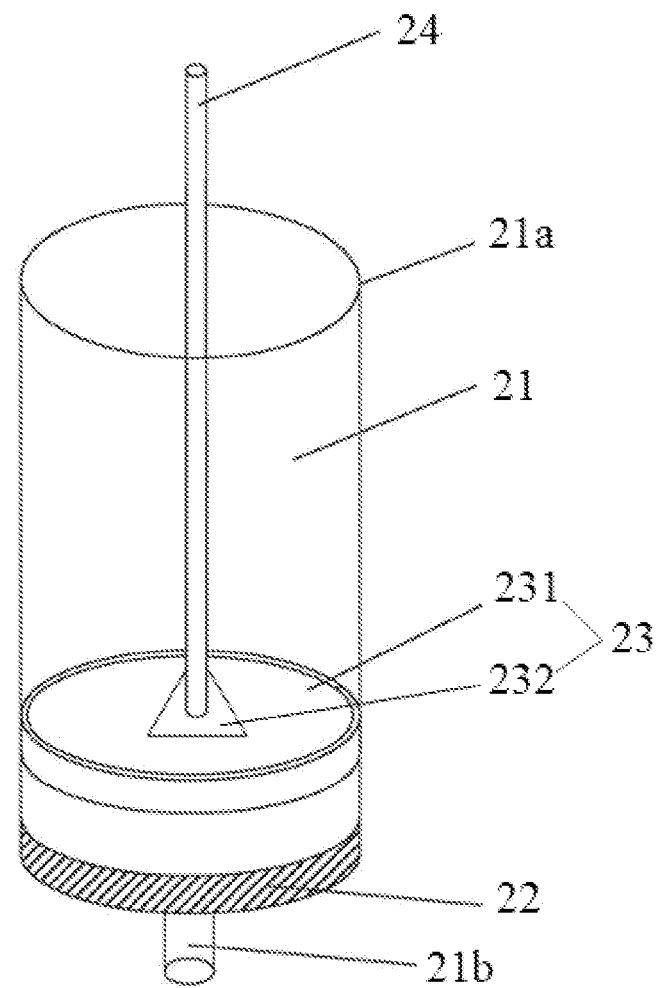
FIG. 6 is a schematic structural view of a biochemical molecule extraction and purification device provided by an embodiment of the present application.

As shown in FIG. 6, the biochemical molecule extraction and purification device includes an extraction column 21, an extraction membrane 22, a liquid temporary blocking mechanism 23, and an execution member 24. One end of the extraction column 21 is provided with an extraction column liquid inlet 21a, and the other end of the extraction column 21 is provided with an extraction column liquid outlet 21b. The extraction membrane 22 and the liquid temporary blocking mechanism 23 are both provided in the extraction column 21, and the liquid temporary blocking mechanism 23 is located between the extraction column liquid inlet 21a and the extraction membrane 22.

Figure 7:
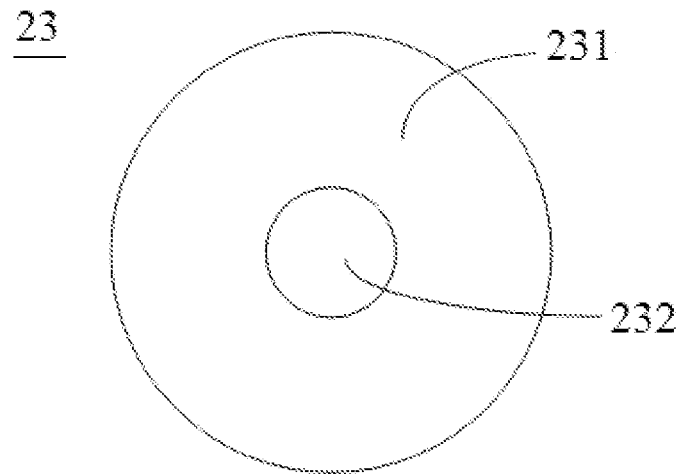
FIGS. 7 to 15 are schematic structural views of a liquid temporary blocking mechanism provided by an embodiment of the present application.

As shown in FIG. 7, the liquid temporary blocking mechanism 23 includes a horizontal supporting portion 231 and at least one detachable portion 232. The horizontal supporting portion 231 is retained on an inner wall of the extraction column 21.

Figure 8:
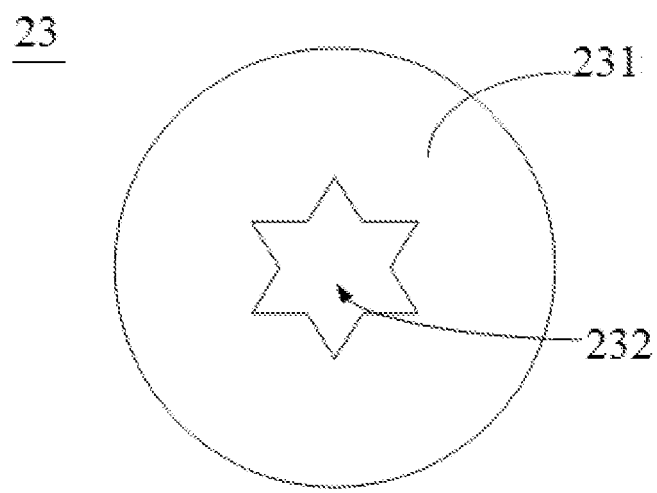

As shown in FIG. 8, the horizontal supporting portion 231 is provided with at least one mounting hole 21c. The number of the mounting holes 21c is the same as the number of the detachable portions 232, and one detachable portion 232 is provided in each mounting hole 21c. The detachable portion 232 is matched with the execution member 24 and can be detached from the corresponding mounting hole 21c under the action of the execution member 24.

By providing the liquid temporary blocking mechanism 23, which includes the horizontal supporting portion 231 and at least one detachable portion 232 installed in the corresponding mounting hole 21c on the horizontal supporting portion 231, between the extraction column liquid inlet 21a of the extraction column 21 and the extraction membrane 22, the liquid temporary blocking mechanism 23 and the extraction column 21 form a liquid storage cavity while each detachable portion 232 is located in the corresponding mounting hole 21c, the extraction column 21 has the function of a test tube, so that the device can contain liquid to realize pretreatment of nucleic acid extraction and purification, namely the process of cell rupture. After the detachable portion 232 is detached from the corresponding mounting hole 21c under the action of the execution member 24, the corresponding mounting hole 21c forms a leakage hole, the liquid containing nucleic acids flows down through the leakage hole, and the nucleic acids are extracted and purified by the extraction membrane 22. In this process, the liquid is transferred from the liquid storage cavity to the extraction membrane 22, thus realizing rapid and simple transfer of the liquid. In the device, the liquid transfer process neither requires manual cooperation with a pipette nor an automated robotic arm or a mechanical pipette to complete the liquid transfer process. The device greatly reduces the cost of nucleic acid and other molecule extraction and accelerates the extraction and purification. Compared with manual pipetting, the workload of operators on nucleic acid extraction and purification is reduced, and the difficulty of nucleic acid extraction and purification is reduced too. Besides, the device is small, light, and cost saving, thereby improving the efficiency of nucleic acid extraction and purification.

Exemplarily, the materials for preparing the detachable portion 232 and/or the horizontal supporting portion 231 may be various plastics, rubbers, papers, glasses, leathers, resins, metals or alloys, aluminum foils, and the like.

Two structures of the liquid temporary blocking mechanism 23 are provided in the present embodiment.

In the first structure, the liquid temporary blocking mechanism 23 is composed of only the horizontal supporting portion 231 and the detachable portion 232. According to the structure of the detachable portion 232, the first structure may have two forms (form A and form B). In form A, the detachable portion 232 is sheet-shaped (as shown in FIG. 6). In form B, the detachable portion 232 is a round plug.

In form A, the detachable portion 232 and the horizontal supporting portion 231 are made of the same material and are integrated as one piece, and in this case, the shape of the entire liquid temporary blocking mechanism 23 may be a sheet. The detachable portion 232 may be a round sheet (as shown in FIG. 7), a triangular sheet (as shown in FIG. 6), a snowflake-shaped sheet (as shown in FIG. 8), or the like.

Figure 9:
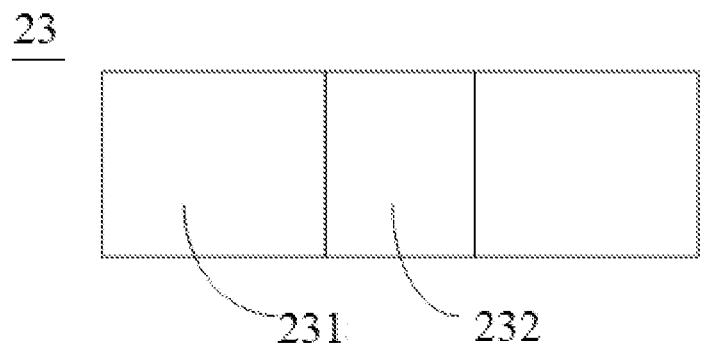

In form B, referring to FIG. 9, the detachable portion 232 is a round plug and the horizontal supporting portion 231 is a cylinder. The outer diameter of the detachable portion 232 is equal to or slightly smaller than the inner diameter of the corresponding mounting hole 21c, and the detachable portion 232 is retained in the corresponding mounting hole 21c. Exemplarily, referring to FIG. 9, the horizontal supporting portion 231 has a certain longitudinal thickness which is the same as the longitudinal thickness of the detachable portion 232. In addition, the bottom of the detachable portion 232 may have one or more protrusions to avoid decrease of the extraction efficiency caused by a lower plane of the detachable portion 232 coming into contact with the nucleic acid extraction membrane 22 after the detachable portion 232 falls off.

Figure 10:
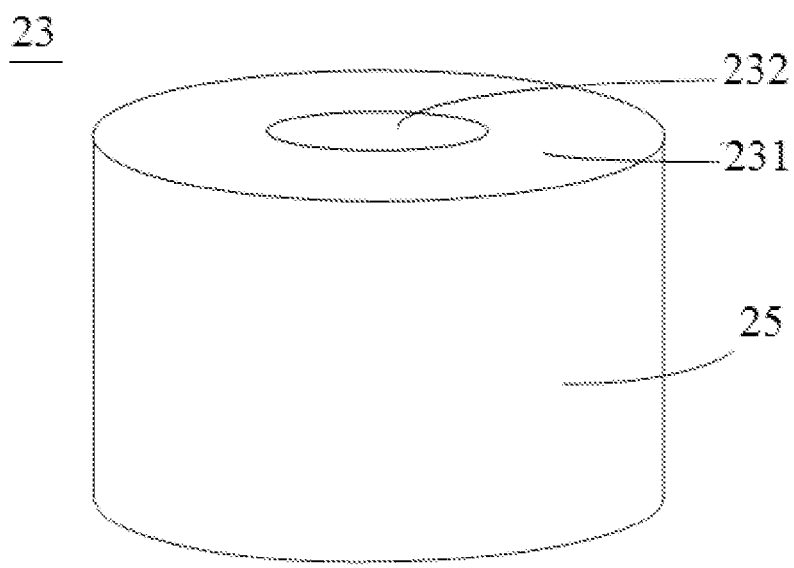
Figure 11:
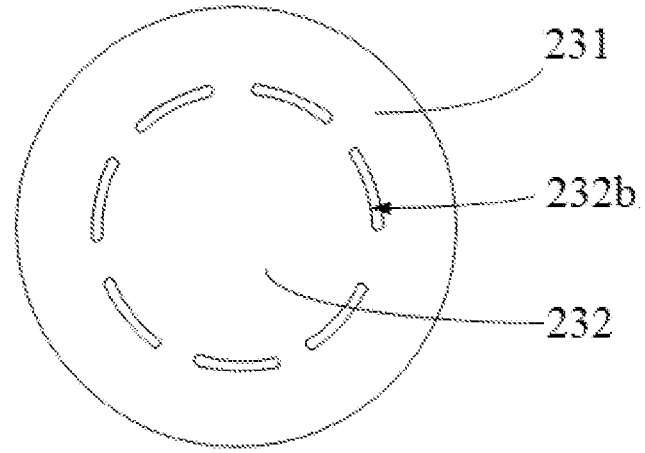

In the second structure, referring to FIG. 10, the liquid temporary blocking mechanism 23 further includes an outer longitudinal supporting portion 25, wherein the outer longitudinal supporting portion 25 is fixed outside the horizontal supporting portion 231 and is perpendicular to the horizontal supporting portion 231. The horizontal supporting portion 231 is retained on the inner wall of the extraction column 21 (as shown in FIG. 6) by the outer longitudinal supporting portion 25. In this case, the liquid temporary blocking mechanism 23 resembles a bottle cap or a cylindrical shape in appearance.

The introduction of the outer longitudinal supporting portion 25 can provide a strong support force. The embodiment of the present application does not limit the fixing manner of the outer longitudinal supporting portion 25 and the horizontal supporting portion 231. Exemplarily, in a case that the materials of the outer longitudinal supporting portion 25 and the horizontal supporting portion 231 are the same, for example, both are plastics, the outer longitudinal supporting portion 25 and the horizontal supporting portion 231 may be integrally formed into a cylindrical shape or other shapes. When the materials of the outer longitudinal supporting portion 25 and the horizontal supporting portion 231 are different, for example, the outer longitudinal supporting portion 25 is made of plastic and the horizontal supporting portion 231 is made of paper. In this case, a clamping member may be adopted to clamp the horizontal supporting portion 231 on the outer longitudinal supporting portion 25. Based on this, the outer longitudinal supporting portion 25 includes an upper ring and a lower ring, and the horizontal supporting portion 231 is clamped between the upper ring and the lower ring. In this way, the outer longitudinal supporting portion 25 adopts a double-ring structure, and the horizontal supporting portion 231 is clamped between the double rings of the outer longitudinal supporting portion 25, so that the horizontal supporting portion 231 can be better fixed.

According to the structure of the detachable portion 232, the second structure may have two forms. In the first form, the detachable portion 232 may be sheet-shaped, and in the second form, the detachable portion 232 may be a round plug.

In the first form, when the detachable portion 232 is sheet-shaped, the detachable portion 232 is easily detached from the mounting hole 21c under the action of the execution member 24. Exemplarily, referring to FIG. 11, the detachable portion 232 is sheet-shaped, and multiple discontinuous first strip-shaped holes 232b are provided between the detachable portion 232 and the horizontal supporting portion 231. In implementation, tiny slits or dotted-line slits of various shapes may be provided between the horizontal supporting portion 231 and the detachable portion 232, and the two are connected with each other and are not completely separated from each other or the two are connected with each other at only a few points and are not separated from each other. The width of the slits is determined according to the specific situation, as long as the molecular solution cannot seep from the slits. Since water molecules have a certain tension, if the slits are too small, water will not seep from the slits in a short period of time, so the width of the slits is associated with the volume and specific gravity of the solution in the column and the pressure generated by the local air pressure on the slits, as well as the time that the solution needs to stay in the column. If the width of the first strip-shaped holes 232b is less than or equal to 0.2 mm, that is, the width of the slits is less than or equal to 0.2 mm, experiments prove that the molecular solution cannot seep from the slits. In addition, while the liquid temporary blocking mechanism 23 with slits is impermeable to liquid (that is, the column can be used as a test tube before the detachable portion 232 is not pierced), the detachable portion 232 can be easily pierced by the execution member 24, which is especially suitable for use in high flux nucleic acid extraction instruments such as 96 flux nucleic acid extraction instruments. Since it may be necessary to pierce multiple (for example, 96) detachable portions 232 in the nucleic acid extraction column 21 in the high flux case, the detachable portions 232 can be easily pierced if the liquid temporary blocking mechanism 23 is of such a structure. That is because the connection between the detachable portions 232 and the horizontal supporting portion 231 is actually partially or mostly in a separated state.

Figure 12:
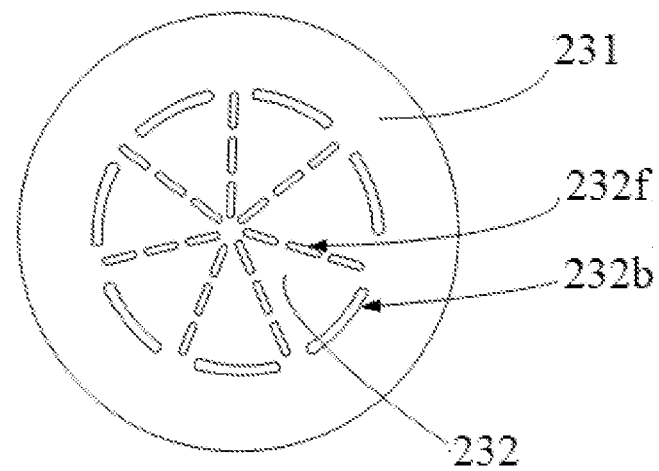
Figure 13:
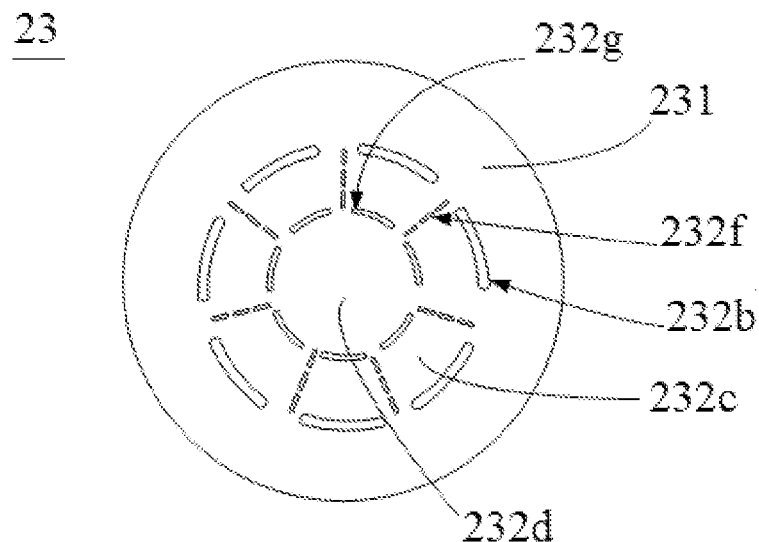
Figure 14:
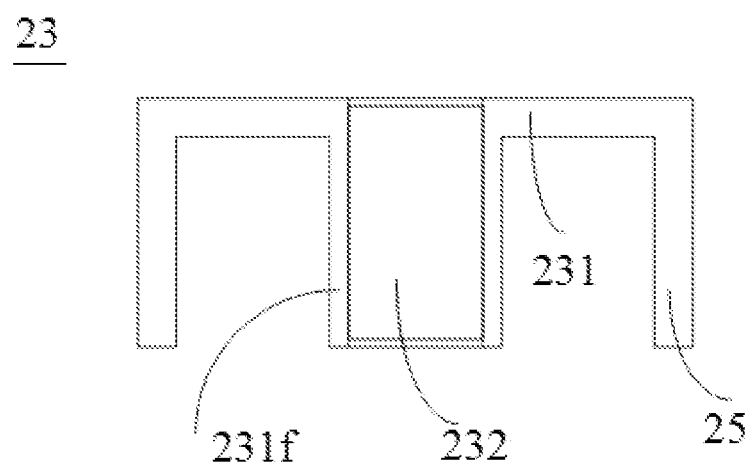

Exemplarily, referring to FIG. 12, the detachable portion 232 is a round sheet, and multiple discontinuous second strip-shaped holes 232f are provided on the detachable portion 232 in the radial direction. After being stressed, the detachable portion 232 is easy to be ruptured at multiple places by the multiple discontinuous second strip-shaped holes 232f, thereby forming a flow channel allowing liquid to pass through.

Correspondingly, in a case that the detachable portion 232 is a round sheet, the horizontal supporting portion 231 is a round sheet, and the horizontal supporting portion 231 and the outer longitudinal supporting portion 5 are integrated into a cylindrical shape or other shapes.

Since the detachable portion 232 is provided with multiple discontinuous second strip-shaped holes 232f in the radial direction, exemplarily, referring to FIG. 12, the detachable portion 232 includes a first outer ring 232c and a first inner ring 232d. The first outer ring 232c is radially provided with the multiple discontinuous second strip-shaped holes 232f, and multiple discontinuous third strip-shaped holes 232g are provided between the first outer ring 232c and the first inner ring 232d.

Exemplarily, the widths of the first strip-shaped hole 232b, the second strip-shaped hole 232f, and the third strip-shaped hole 232g are all less than or equal to 0.2 mm.

In the second form, the detachable portion 232 may be a round plug. Exemplarily, referring to FIG. 14, the detachable portion 232 is a round plug, the horizontal supporting portion 231 is a round sheet, and the liquid temporary blocking mechanism 23 further includes an inner longitudinal supporting portion 231f. The inner longitudinal supporting portion 231f is arranged inside the outer longitudinal supporting portion 25. The inner longitudinal supporting portion 231f is fixed to the inner ring of the horizontal supporting portion 231 and is perpendicular to the horizontal supporting portion 231. The inner longitudinal supporting portion 231f is a cylinder, and the detachable portion 232 is retained in the inner longitudinal supporting portion 231f.

The space between the inner longitudinal supporting portion 231f and the outer longitudinal supporting portion 25 is hollow. In this way, the cylindrical wall of the inner longitudinal supporting portion 231f has horizontal extensibility. When the detachable portion 232 is detached from the hollow cylinder by external force, the inner wall of the inner longitudinal supporting portion 231f can extend toward the outer hollow part to facilitate detachment of the detachable portion 32.

Figure 15:
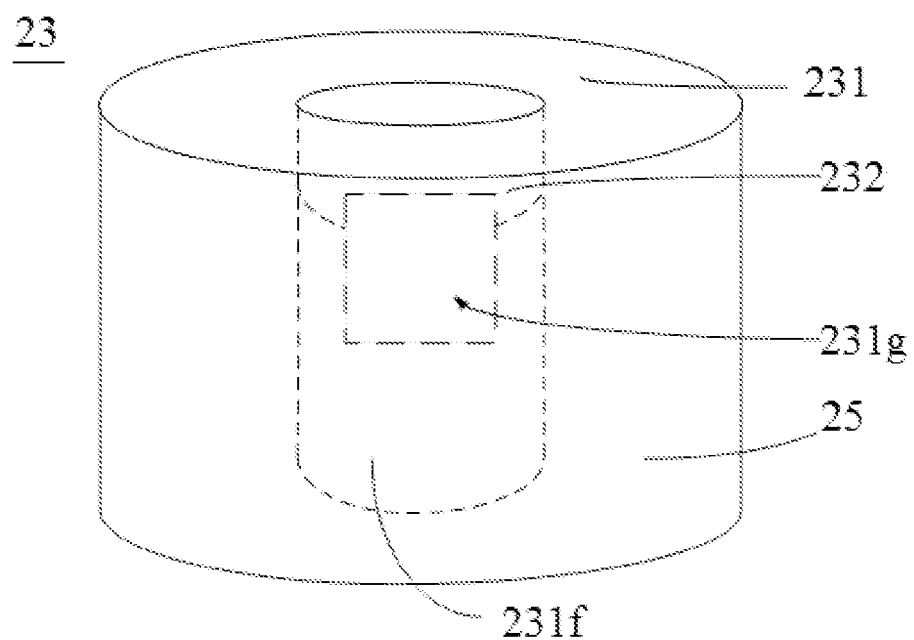

Based on the introduction of the inner longitudinal supporting portion 231f, exemplarily, referring to FIG. 15, the inner longitudinal supporting portion 231f is a bottom-sealed cylinder, the detachable portion 232 is retained at an opening of the inner longitudinal supporting portion 231f, and an inner wall of the inner longitudinal supporting portion 231f is provided with at least one window hole 231g. When detached from the corresponding mounting hole 21c, the detachable portion 232 falls onto the bottom of the bottom-sealed cylinder, and the molecular solution flows out through the window hole 231g. With such a design, the detachable portion 232 is prevented from falling on the extraction membrane 22 and affecting the extraction and purification effect.

In this embodiment, exemplarily, the extraction membrane 22 may be a filter membrane or an absorption membrane. The execution member 24 may be a rod.

An exemplary working process of the biochemical molecule extraction and purification device provided in this embodiment is briefly described in the following, which is as follows. The user adds liquid cells and various chemical reagents (such as cell lysis solution) into the extraction column 21, mixes them well by the execution member 24 and then left them to stand still. After the cells are ruptured, the nucleic acids in the cells are released into the solution to form a nucleic acid solution to be extracted and purified. Part or all of the detachable portions 232 are detached from the mounting holes 21c by the execution member 24, so that the nucleic acid solution to be extracted flows down onto the extraction membrane 22 through the mounting holes 21c. Here, impurities are filtered out by the extraction membrane 22 (filter membrane) or nucleic acids are absorbed by the extraction membrane 22 (absorption membrane), and then the extraction membrane 22 is rinsed and eluted to extract the nucleic acids. The device is not only suitable for the extraction and purification of the nucleic acid molecules, but also suitable for the extraction and purification of various biochemical molecules.

The foregoing shows only preferred embodiments of the present application and is not intended to limit the present application, and any modifications, equivalent substitutions and improvements within the spirit and the principle of the present application are included within the protection scope of the present application.

The invention claimed is:

1. A nucleic acid extraction and purification device, comprising a nucleic acid purification column and a breakable member, wherein
 a purification column liquid inlet is provided at the top of the nucleic acid purification column, a purification column liquid outlet is provided at the bottom of the nucleic acid purification column, and a nucleic acid extraction membrane is provided in the nucleic acid purification column; and
 the breakable member is arranged between the purification column liquid inlet and the nucleic acid extraction membrane, and is arranged in the nucleic acid purification column, the breakable member is provided with a groove, and the nucleic acid extraction and purification device further comprises a piercing rod for piercing the breakable member,
 wherein the groove comprises an annular groove arranged at the center of the breakable member, and a plurality of support legs are provided on a bottom surface of the breakable member on the annular groove.

2. The nucleic acid extraction and purification device according to claim 1, wherein the groove comprises a plurality of strip-shaped grooves arranged along a radius of the breakable member.

3. The nucleic acid extraction and purification device according to claim 1, wherein the nucleic acid extraction and purification device further comprises a support member, the support member is hermetically installed on an inner wall of the nucleic acid purification column, and the breakable member is fixed to the support member.

4. The nucleic acid extraction and purification device according to claim 3, wherein the support member is a cylinder, or a round sheet with a hole in the middle, or a round basin with a basin bottom facing upward and a hole in the middle of the basin bottom; and
 the breakable member is sheet-shaped, and is bonded with the support member by hot melting.

5. The nucleic acid extraction and purification device according to claim 3, wherein
 the support member comprises a round basin with a basin bottom facing upward and a hole in the middle of the basin bottom, and further comprises a snap ring, the snap ring comprises an annular body and an annular snap protrusion arranged on an outer periphery of the annular body, a peripheral wall of the round basin is provided with an annular snapping groove adapted to the annular snapping protrusion, and the snap ring is snapped and installed in the round basin; and
 the breakable member is sheet-shaped, and is clamped between an upper end surface of the annular body and a lower end surface of the basin bottom.

6. The nucleic acid extraction and purification device according to claim 5, wherein one of the lower end surface of the basin bottom and the upper end surface of the annular body is provided with an annular groove, the other is provided with a protrusion adapted to the annular groove,
 the breakable member is provided with a bulging portion adapted to the annular groove, and the protrusion is configured to press the bulging portion into the annular groove.

7. The nucleic acid extraction and purification device according to claim 5, wherein an inner edge of the upper end surface of the basin bottom is inclined downward relative to an outer edge of the upper end surface, and an inner edge of the lower end surface of the annular body is inclined upward relative to an outer edge of an outer edge of the lower end surface.

8. The nucleic acid extraction and purification device according to claim 1, wherein the nucleic acid extraction and purification device further comprises a mounting column, the mounting column is sleeved on an inner wall of the nucleic acid purification column, and the breakable member is provided on the mounting column and located above the nucleic acid extraction membrane.

9. The nucleic acid extraction and purification device according to claim 1, wherein the bottom of the piercing rod has a conical structure, a lower part of the piercing rod is sleeved with a stirring sheet, and an outer diameter of the stirring sheet is smaller than an inner diameter of the nucleic acid purification column.

10. The nucleic acid extraction and purification device according to claim 1, wherein the breakable member is a polypropylene breakable member, a polyethylene breakable member, a polytetrafluoroethylene breakable member, an acetate breakable member, a nitrocellulose breakable member, or a regenerated fiber breakable member.

11. The nucleic acid extraction and purification device according to claim 1, wherein a ratio of a depth of the groove to a thickness of the breakable member is 100:(101 to 1150).

* * * * *